US00PP22676P2

(12) United States Plant Patent
Hooijman

(10) Patent No.: US PP22,676 P2
(45) Date of Patent: Apr. 24, 2012

(54) ROSE PLANT NAMED 'ESM KATA'

(50) Latin Name: *Rosa hybrida*
Varietal Denomination: Esm Kata

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 12 days.

(21) Appl. No.: 12/807,253

(22) Filed: Aug. 31, 2010

(51) Int. Cl.
*A01H 5/00* (2006.01)

(52) U.S. Cl. ..... Plt./132

(58) Field of Classification Search ..... Plt./132, Plt./130, 143
See application file for complete search history.

(56) References Cited

OTHER PUBLICATIONS

Upov-rom Plt Var Database 2011/01, Citation for Rosa 'Esm Kata', one page.*

* cited by examiner

*Primary Examiner* — June Hwu
(74) *Attorney, Agent, or Firm* — C. A. Whealy

(57) ABSTRACT

A new and distinct cultivar of Rose plant named 'Esm Kata', characterized by its long, strong and upright flowering stems; durable glossy foliage; light yellow green-colored flowers with red-colored margins; good postproduction longevity; and resistance to Botrytis, Powdery Mildew and spider mites.

1 Drawing Sheet

Botanical designation: *Rosa hybrida.*
Cultivar denomination: 'ESM KATA'.

BACKGROUND OF THE INVENTION

The present Invention relates to a new and distinct cultivar of Rose plant, botanically known as *Rosa hybrida,* commercially used as a cut flower Rose plant, and hereinafter referred to by the name 'Esm Kata'.

The new Rose plant is a product of a planned breeding program conducted by the Inventor in El Quinche, Pichincha, Ecuador. The objective of the breeding program was to develop new freely-flowering cut flower Rose varieties with novel and attractive flower colors and excellent postproduction longevity.

The new Rose plant originated from a cross-pollination made by the Inventor in February, 2000 of a proprietary Rose selection identified as code name Line 95, not patented, as the female, or seed, parent with a proprietary Rose selection identified as code name Line 51, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in March, 2001.

Asexual reproduction of the new Rose plant by cuttings at El Quinche, Pichincha, Ecuador since April, 2001, has shown that the unique features of this new Rose plant are stable and reproduced true to type in successive generations of asexual reproduction.

SUMMARY OF THE INVENTION

Plants of the new Rose have not been observed under all possible environmental conditions. The phenotype may vary somewhat with variations in environment such as temperature and light intensity, without, however, any variance in genotype.

The following traits have been repeatedly observed and are determined to be the unique characteristics of 'Esm Kata'. These characteristics in combination distinguish 'Esm Kata' as a new and distinct Rose plant:

1. Long, strong and upright flowering stems.
2. Durable glossy foliage.
3. Light yellow green-colored flowers with red-colored margins.
4. Good postproduction longevity.
5. Resistant to Botrytis, Powdery Mildew and spider mites.

Plants of the new Rose differ from plants of the female parent selection in the following characteristics:

1. Plants of the new Rose have larger flowers than plants of female parent selection.
2. Plants of the new Rose and the female parent selection differ in flower color as plants of the female parent selection have cream and pink bi-colored flowers.

Plants of the new Rose differ from plants of the male parent selection in the following characteristics:

1. Plants of the new Rose are larger than plants of the male parent selection.
2. Plants of the new Rose are more freely flowering than plants of the male parent selection.
3. Plants of the new Rose and the male parent selection differ in flower color as plants of the male parent selection have orange and yellow bi-colored flowers.

Plants of the new Rose can be compared to plants of Rose 'Super Green', not patented. In side-by-side comparisons conducted in El Quinche, Pichincha, Ecuador, plants of the new Rose differed from plants of 'Super Green' in the following characteristics:

1. Plants of the new Rose were larger and more vigorous than plants of 'Super Green'.

2. Plants of the new Rose had thicker and stronger stems than plants of 'Super Green'.
3. Plants of the new Rose had fewer thorns plants of 'Super Green'.
4. Plants of the new Rose had smaller flowers than plants of 'Super Green'.
5. Plants of the new Rose had fewer petals per flower than plants of 'Super Green'.
6. Plants of the new Rose and 'Super Green' differed in flower color as plants of 'Super Green' had green-colored flowers.
7. Flowers of plants of the new Rose were longer lasting than flowers of plants of 'Super Green'.

BRIEF DESCRIPTION OF THE PHOTOGRAPH

The accompanying colored photograph illustrates the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph at the upper left of the sheet comprises a side perspective view of a typical flowering stem of 'Esm Kata'.

The photograph at the lower left of the sheet is a close-up view of typical flowers of 'Esm Kata'.

The photograph at the top right of the sheet is a close-up top perspective view of a typical flower of 'Esm Kata'.

The photographs at the lower right of the sheet are close-up views of the upper and lower surfaces of typical leaves of 'Esm Kata'.

DETAILED BOTANICAL DESCRIPTION

Plants of the new Rose have not been observed under all possible environmental conditions. The phenotype may vary somewhat with variations in environment such as temperature and light intensity, without, however, any variance in genotype. The aforementioned photographs, following observations and measurements describe plants grown in ground beds in a polyethylene-covered greenhouse in El Quinche, Pichincha, Ecuador and under commercial Rose production practices. Plants were pinched about 13 to 14 weeks after planting. Plants were 2.5 years old when the photographs and description were taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2001 Edition, except where general terms of ordinary dictionary significance are used.

Botanical classification: *Rosa hybrida* 'Esm Kata'.

Parentage:

*Female, or seed, parent.*—Proprietary seedling selection of *Rosa hybrida* identified as code name Line 95, not patented.

*Male, or pollen, parent.*—Proprietary seedling selection of *Rosa hybrida* identified as code name Line 51, not patented.

Propagation:

*Type.*—By cuttings.

*Time to initiate roots.*—About seven to ten days at 26° C. to 30° C.

*Time to produce a rooted young plant.*—About four to five weeks at 22° C. to 26° C.

*Root description.*—Fibrous, thick; close to 200C in color.

*Rooting habit.*—Freely branching; moderately dense.

Plant description:

*Plant form.*—Upright plant habit; long, strong and upright flowering stems.

*Growth habit.*—Vigorous; freely basal branching habit; dense and bushy growth habit; about 14.4 flowering stems develop per year.

*Plant height.*—About 100 cm to 117 cm.

*Plant width (spread).*—About 62 cm.

*Lateral branches (peduncles).*—Length: About 70 cm. Diameter: About 6.4 mm. Internode length: About 3.7 cm. Texture: Smooth, glabrous. Color: Close to 146A and 148A. Thorns: Density: Low. Shape: Triangular with sharp acuminate apices. Height: About 9.6 mm. Length, at base: About 6.3 mm. Color, immature: Close to 185A. Color, mature: Close to 166B.

Foliage description:

*Arrangement.*—Alternate; compound with typically three to five glossy leaflets per leaf.

*Leaf length.*—About 15.3 cm.

*Leaf width.*—About 12 cm.

*Terminal leaflet length.*—About 7 cm.

*Terminal leaflet width.*—About 5.5 cm.

*Lateral leaflet length.*—About 5.7 cm.

*Lateral leaflet width.*—About 4.4 cm.

*Leaflet shape.*—Oval.

*Leaflet apex.*—Acute.

*Leaflet base.*—Attenuate.

*Leaflet margin.*—Serrate.

*Leaflet texture, upper and lower surfaces.*—Smooth, glabrous.

*Leaflet venation pattern.*—Pinnate.

*Leaflet color.*—Developing leaflets, upper surface: Close to 147A tinged with close to N186C. Developing leaflets, lower surface: Close to 146C tinged with close to 166A. Fully expanded leaflets, upper surface: Close to 147A and 139A; venation, close to 148A. Fully expanded leaflets, lower surface: Close to 147B; venation, close to 146C.

*Petioles, leaves.*—Length: About 2 cm. Diameter: About 1.8 mm. Texture, upper and lower surfaces: Pubescent. Color, upper surface: Close to 146A to 146C. Color, lower surface: Close to 144A.

*Petioles, leaflets.*—Length: About 2.2 cm. Diameter: About 1.4 mm. Texture, upper and lower surfaces: Pubescent. Color, upper surface: Close to 146A tinged with close to 200A. Color, lower surface: Close to 144A.

*Stipules.*—Quantity/arrangement/appearance: Two, adnate to the petiole, leafy. Length: About 2.1 cm. Width: About 2.2 mm. Shape: Roughly deltoid. Apex: Acuminate. Base: Truncate. Margin: Serrate, irregular. Texture, upper and lower surfaces: Pubescent. Venation pattern: Pinnate. Color, upper surface: Close to 146A. Color, lower surface: Close to 148A.

Flower description:

*Flower type and habit.*—Symmetrical rosette flowers; typically grown as a single stem.

*Flowering season.*—Year-round under greenhouse conditions, plants begin flowering about 65 to 67 days after planting; in the garden, optimal flowering from spring through autumn; flowering intermittent.

*Flower diameter.*—About 8.4 cm.

*Flower depth* (*height*).—About 4.3 cm.

*Flower longevity on plant.*—About 34 days; flowers persistent.

*Flower longevity as a cut flower.*—About 14 days.

*Fragrance.*—Slightly fragrant, pleasant.

*Flower buds.*—Shape: Urn-shaped. Length: About 4.8 cm. Diameter: About 4.6 cm. Color: Close to 144A tinged with close to 183A.

*Petals.*—Quantity: About 32 per flower; petals imbricate. Length: About 4.5 cm. Width: About 4.8 cm. Shape: Nearly round; transversely ovate. Apex: Blunt to acute. Base: Obtuse. Margin: Entire. Texture, upper and lower surfaces: Smooth, glabrous. Color: When opening, upper surface: Close to 154D; towards the base, close to 2A; towards the margins, close to 48B and 54B. When opening, lower surface: Close to 1D; towards the base, close to 2A; towards the margins, close to 53B. Fully opened, upper surface: Close to 150D; towards the base, close to 154B; towards the margins, close to 53C and 54B. Fully opened, lower surface: Close to 150D; towards the base, close to 154C; towards the margins, close to 54B and 53A.

*Sepals.*—Quantity per flower: Typically five. Length: About 4.8 cm. Width: About 1.3 cm. Shape: Roughly deltoid. Apex: Tapered. Base: Truncate. Margin: Entire; ciliate. Texture, upper and lower surfaces: Pubescent; leathery. Color: When opening, upper surface: Close to 146B. When opening, lower surface: Close to 146A tinged with close to 166A. Fully opened, upper surface: Close to 146B to 146D. Fully opened, lower surface: Close to 144A tinged with close to 183B.

*Reproductive organs.*—Stamens: Quantity: About 146 per flower. Anther length: About 3 mm. Anther shape: Reniform. Anther color: Close to 153D. Filament color: Close to 153D. Pollen amount: Scarce. Pollen color: Close to 17A. Pistils: Quantity: About 135 per flower. Pistil length: About 1.4 cm. Stigma shape: Broadly reniform. Stigma color: Close to 153D. Style length: About 8.6 mm. Style color: Close to 155C. Receptacle height: About 1.1 cm. Receptacle diameter: About 1.2 cm. Receptacle shape: Cup-shaped. Receptacle texture: Smooth, glabrous. Receptacle color: Close to 144A. Fruits and seeds: Fruit and seed development have not been observed on plants of the new Rose.

Pathogen/pest resistance: Plants of the new Rose have been observed to be resistant to Botrytis, Powdery Mildew and spider mites. Plants of the new Rose have not been observed to be resistant to other pathogens and pests common to Roses.

Temperature tolerance: Plants of the new Rose have been observed to tolerate temperatures ranging from 0° C. to 35° C.

It is claimed:

1. A new and distinct Rose plant named 'Esm Kata' as illustrated and described.

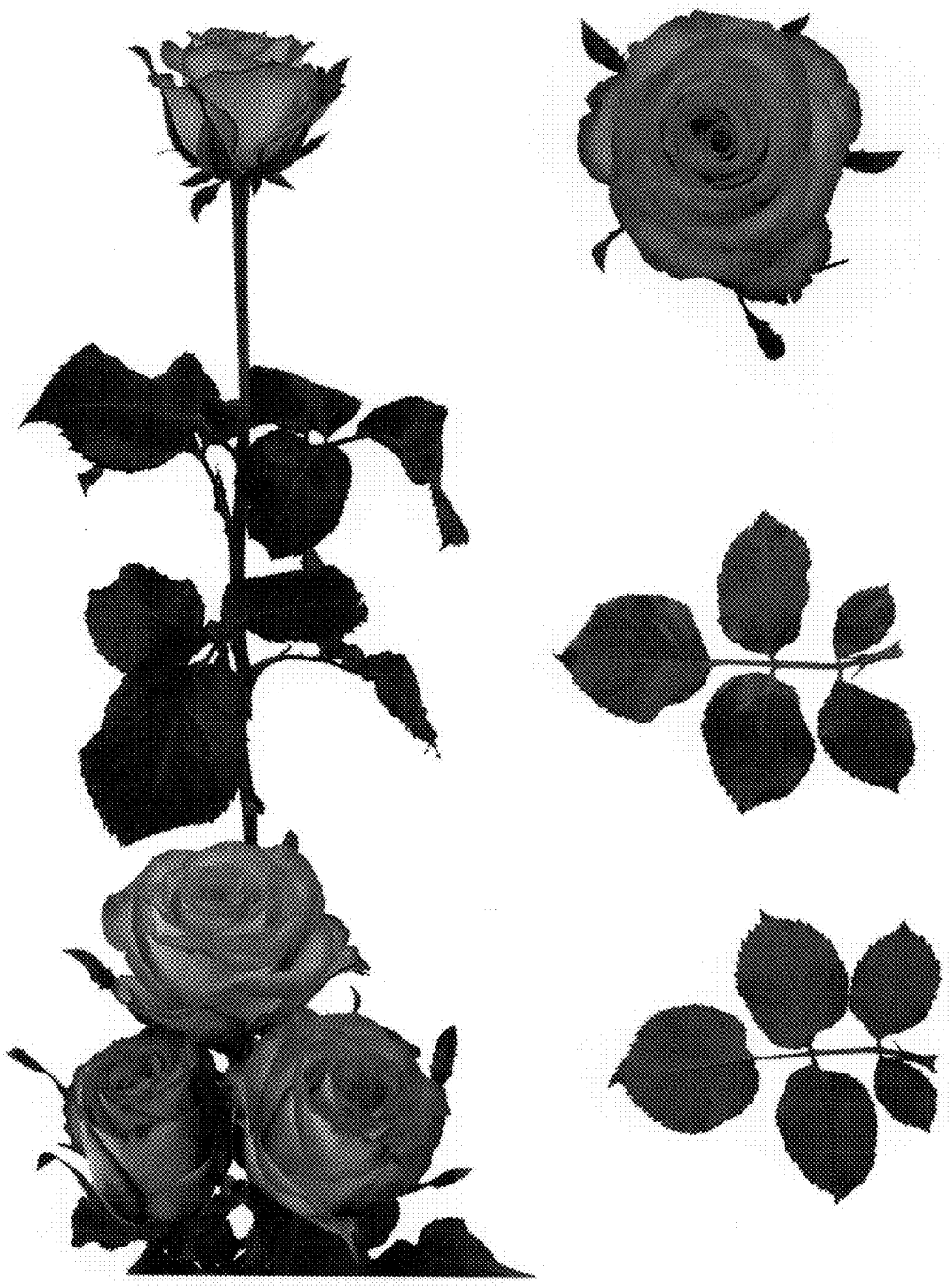

* * * * *